United States Patent [19]

Maekawa et al.

[11] 4,250,166

[45] Feb. 10, 1981

[54] LONG ACTING PREPARATION OF CEFALEXIN FOR EFFECTIVE TREATMENTS OF BACTERIAL INFECTION SENSITIVE TO CEFALEXIN

[75] Inventors: Hideyuki Maekawa, Osaka; Yasushi Takagishi, Nishinomiya; Hiroshi Kato, Kobe, all of Japan

[73] Assignee: Shionogi & Co., Ltd., Osaka, Japan

[21] Appl. No.: 801,402

[22] Filed: May 27, 1977

[51] Int. Cl.$^3$ ................... A61K 31/78; A61K 31/54
[52] U.S. Cl. ................................... 424/81; 424/246
[58] Field of Search .......................... 424/246, 81

[56] References Cited

U.S. PATENT DOCUMENTS 3,078,216   2/1963   Grief .................................. 424/19

FOREIGN PATENT DOCUMENTS 644754   5/1937   Fed. Rep. of Germany .
1767320   9/1971   Fed. Rep. of Germany .
2259646   6/1974   Fed. Rep. of Germany ........... 424/246

OTHER PUBLICATIONS

Derwent 02444U, Abstracting, DT-OS 2135073, published Oct. 16, 1972.
Derwent 47983R-AB, Abstracting DT-1814669-Q, published Jul. 2, 1970.
Austria Codex 1974/1975, 1975, pp. 130 & 365.
Derwent #1643T, Abstracting DT 2030501, published Dec. 30, 1971.
Derwent 65478W/39, Abstracting US 3906086, published Sep. 15, 1975.
Derwent 762040-B, Abstracting DT 2325410Q, published May 18, 1973.
Derwent 43846T, Abstracting BE-777158Q, published Jun. 22, 1972.
Derwent 81270V, Abstracting DT-2421273, published Nov. 14, 1974.
Derwent S9394S, Abstracting FR-2059978-Q, published Jun. 11, 1971.

*Primary Examiner*—Jerome D. Goldberg
*Attorney, Agent, or Firm*—Wenderoth, Lind & Ponack

[57] ABSTRACT

A cefalexin preparation coated with a coating layer the solubility of which layer is pH-dependent and dissolves in the upper intestine is preferably administered concurrently with a normal (plain, quick-releasing) cefalexin. The coated preparation is preferably coated, in the particle form and when administered orally, exists in the particle form in the stomach. Preferably, the coating layer is made from a coating material having a dissolution pH of from 5.5 to 6.5, and the ratio in terms of potency of the coated cefalexin to the normal cefalexin is between 15:85 and 60:40. The coated cefalexin and the normal cefalexin can be formulated in a pharmaceutical preparation preferably in a unit-dosage form, e.g., capsules, tablets or particles or in strip-packages.

14 Claims, 15 Drawing Figures

Blood levels obtained by administering normal cefalexin.
A: 400 mg.
B: 300 mg.
C: 200 mg.

Percentages of the core cefalexin dissolved after one hour from three tyeps of enteric preparations.

Urinary excretion of cefalexin following administration of the three types of enteric preparations of Fig. 4A.

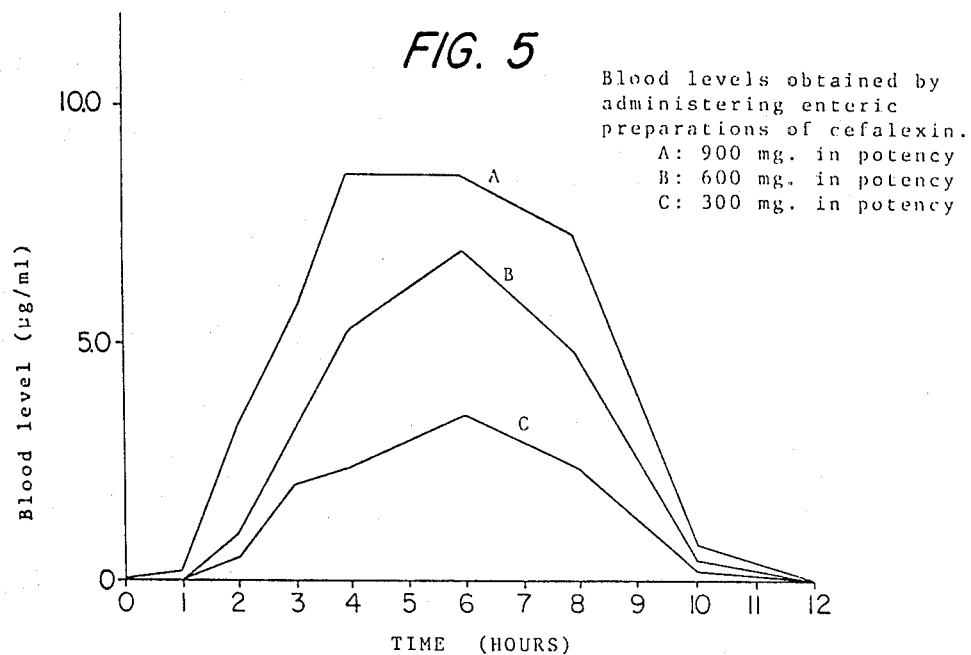
FIG. 5
Blood levels obtained by administering enteric preparations of cefalexin.
A: 900 mg. in potency
B: 600 mg. in potency
C: 300 mg. in potency
Durations of MIC obtained by the combined preparations.
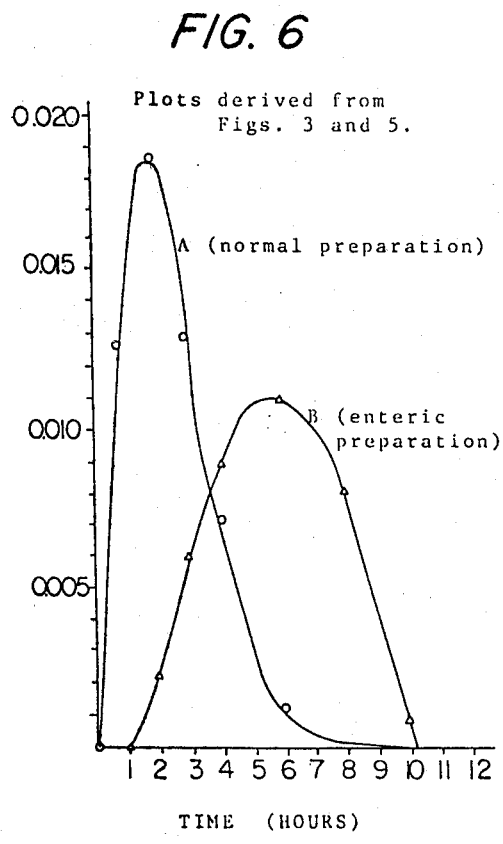
FIG. 6
Plots derived from Figs. 3 and 5.
A (normal preparation)
B (enteric preparation)
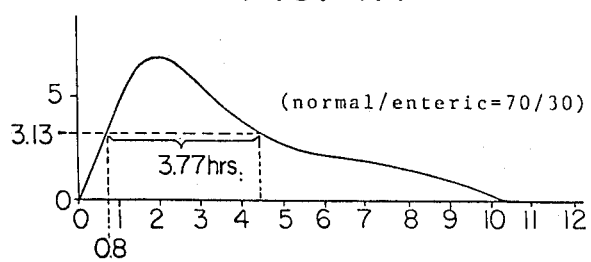
FIG. 7A (normal/enteric=70/30)
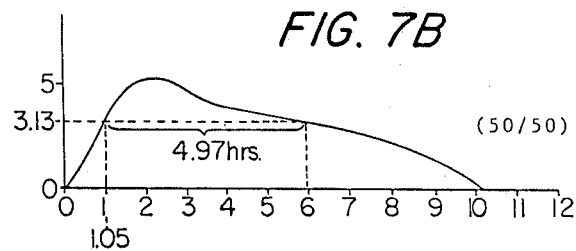
FIG. 7B (50/50)
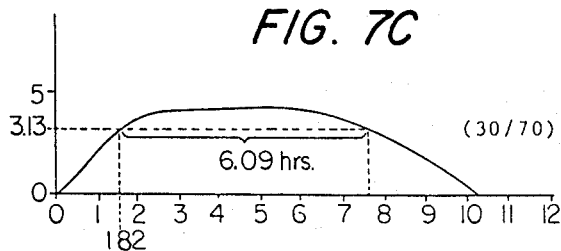
FIG. 7C (30/70)

Percentages in potency of normal/enteric cefalexin in the preparation

A: Durations of blood level of 3.13 µg/ml.
B: Time lags before reaching the blood level of 3.13 µg/ml.

Blood levels obtained upon administering cefalexin preparation of: A (1000 mg), B (500 mg) potency ratio normal to enteric of 30/70, C (2×500 mg), D (2×250 mg) of normal cefalexin.

Blood levels obtained upon administering Cefalexin preparation of : A (1000 mg), B (500 mg) potency ratio normal to enteric of 30/70.
C (500 mg), D (250 mg) of normal cefalexin.

Blood levels obtained upon administering Cefalexin preparation of : A (1000 mg), B (500 mg) potency ratio normal to enteric of 30/70.
C (500 mg), D (250 mg) of normal cefalexin.

LONG ACTING PREPARATION OF CEFALEXIN FOR EFFECTIVE TREATMENTS OF BACTERIAL INFECTION SENSITIVE TO CEFALEXIN

BACKGROUND OF THE INVENTION

This invention relates to a long-acting preparation of cefalexin. Cefalexin [7-D-2-amino-2-phenylacetamido)-3-methyl-3-cephem-4-carboxylic acid monohydrate] has been used widely. It is one of the few oral cephalosporins to be marketed. It is effective against many infections, and is rapidly and for the most part absorbed through the digestive organ. A major portion is excreted in urine without being subjected to any biotransformation in the body.

However, the rapid decrease in its blood level after 1 to 2 hours from administration requires a patient to take the drug usually more than four times a day for an efficient therapy.

This problem is solved by the present invention by making a long-acting preparation of cefalexin comprising normal cefalexin and a coated cefalexin which is effective, safe and convenient for a patient, enabling twice daily administration of the drug, i.e., at 12 hour intervals, which effectively avoids possible interruption of patient's sleep.

In other words, it has now been found that one of the methods for maintaining the necessary blood level of cefalexin in man for a required period comprises the administration of normal and slowly releasing cefalexin preparations practically at the same time.

SUMMARY OF THIS INVENTION

[I] The preparation of this invention comprises (a) cefalexin preparation coated with a coating material the solubility of which is pH-dependent and which dissolves in the upper intestine and (b) normal cefalexin.

Preferable preparations of this invention are composed of the following constituents:

(1) From 60 to 15% (preferably 30%) in terms of the potency of cefalexin;

(2) from 40 to 85% (preferably 70%) in terms of the potency of a coated cefalexin preparation which is coated with a pH dependent coating material having a dissolution pH of 5.5 to 6.5 (preferably about 6.0); and (3) if required, pharmaceutically acceptable carriers or additives in addition to said cefalexin preparations (1) and (2).

Each of the cefalexin preparations (1) and (2) may be in the form of granules or powder, and particularly the coated preparation (2) is preferably coated in the particle form and, when administered orally, exists in the coated form in the stomach. Although the size of the particle is not critical, the maximum weight of one particle does not preferably exceed about 10 milligrams before coating.

The preparation of this invention can be in a unit-dosage form of capsules or tablets containing the said two cefalexin preparations in the potency ratio specified in (1) and (2).

"The unit-dosage form" defined here is a single prescription dose or a fraction thereof.

The preparation of the invention may be formed by compressing the coated cefalexin preparation (2) into a tablet by employing a suitable binding agent. In such a case, portions of the coating layer of the coated preparation are broken to expose core cefalexin and, when disintegrated in gastric juice, to diffuse a portion (about 25–40% of the total tablet), of the cefalexin out but the retained portion of the coated preparation travels gradually to the upper intestine.

[II] The method of this invention comprises treating a bacterial infection in man with an effective amount of normal cefalexin and the coated cefalexin preparation preferably in the ratio specified above in (1) and (2).

"Normal cefalexin" specified above and used throughout this specification means any quick-releasing cefalexin preparation as conventionally used clinically. Usually, it is crystals, powdered crystals, granules, or beads of cefalexin, or if required, a mixture with a pharmaceutical carrier, additive or like excipient. It may further be coated with a layer soluble in gastric juice.

BRIEF DESCRIPTION OF THE DRAWINGS

Each of FIGS. 1 and 2 is a graph representing the bactericidal action of cefalexin in vitro in terms of its dependence upon exposure time; the hatched traversing bars in FIG. 2 indicate exposure levels of cefalexin and their duration, FIG. 5 is a graph similar to FIG. 3, wherein enteric-coated cefalexin preparations are administered, and blood levels determined, FIG. 6 is a graph wherein the plots are derived from FIGS. 3 and 5 indicating blood levels which would be obtained with 1 mg of cefalexin. The two curves are delineated by model equations devised by mathematical simulation, Each of FIGS. 7A, 7B and 7C is a graph derived from the information contained in FIG. 6, indicating the calculated blood levels resulting from administration of various ratios of coated and normal cefalexin and the duration of a desired blood level above 3.13 $\mu$g/ml, FIG. 8 contains curves A and B, the former indicating the duration of blood levels of 3.13 $\mu$g/ml. the latter indicating the time lag required for attaining this blood level obtained by combined dosage-forms in various potency ratios over the full range, FIGS. 9-1 and 9-2 are similar graphs, indicating corrections on FIG. 9 and the results of similar investigation, respectively.

DETAILED DESCRIPTION OF THE INVENTION

1. Time-dependency of bactericidal action in vitro

In contrast to the presently prevailing belief that the bactericidal action of an antibiotic agent is proportional to its concentration or at least the concentration integrated by its exposure time, the present inventors have confirmed the undermentioned facts peculiar to cefalexin through the results of a series of bacterial growth inhibitory experiments. Typical results of these experiments are summarized in FIGS. 1 and 2.

The results of the tests conducted support the following facts:

(a) Exposure to cefalexin over a period of more than 3 hours is necessary for decreasing the number of viable cells of Staphylococcus aureus 209P (ATCC 6538P). The Minimum Inhibitory Concentration (MIC) of cefalexin against this strain is 3.13 μg/ml, according to the standard method recommended by Japan Society of Chemotherapy.

Figure 1:
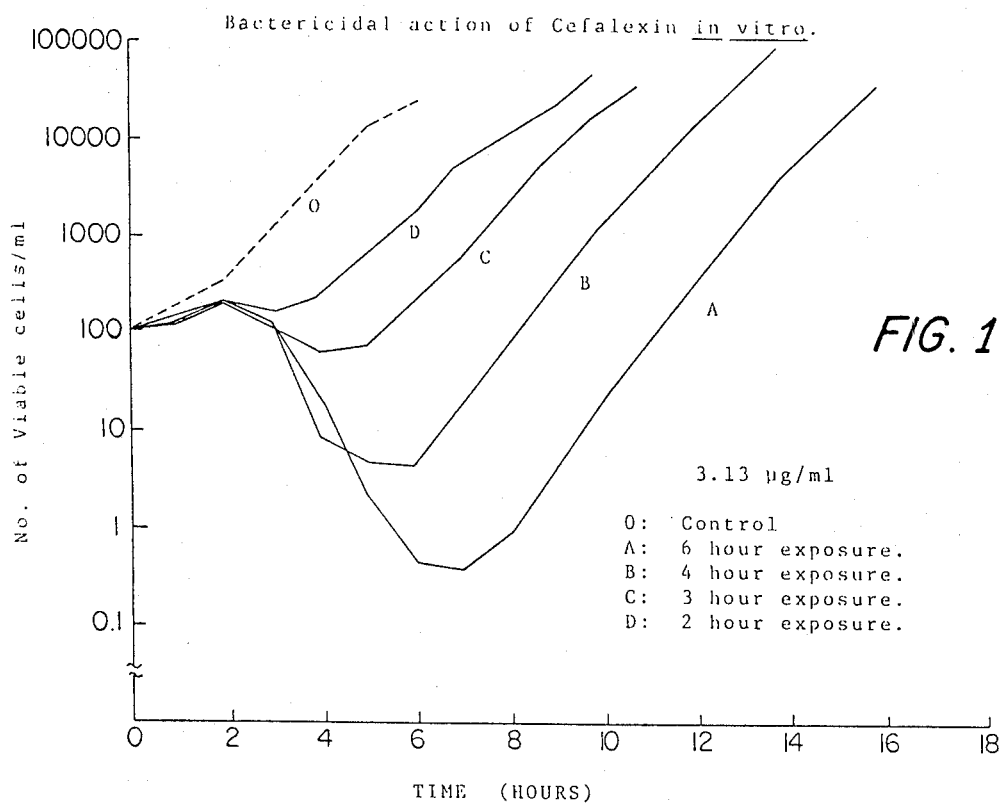

(b) Exposure of the bacteria to 3.13 μg/ml of cefalexin for up to 3 hours is much less effective than exposure for 4 hours or more. Critical exposure time has been found to be between 4 and 6 hours (FIG. 1).

(c) Similar observation was experienced in an experiment with cefalexin concentration of 12.5 μg/ml (4×MIC).

(d) Concurrently performed experiments indicated similar results with 9 additional microorganism strains which belong to *S. aureus* including *Staphylococcus aureus* No. 120160 (a clinical isolate) and with 6 strains which belong to *Escherichia coli*. These results are however considered to be ancillary and therefore are omitted from the instant description for the sake of brevity.

(e) In a short exposure period (up to 6 hours), the decrease in the number of viable cells did not show the expected clear response to the concentration of cefalexin.

Figure 2:
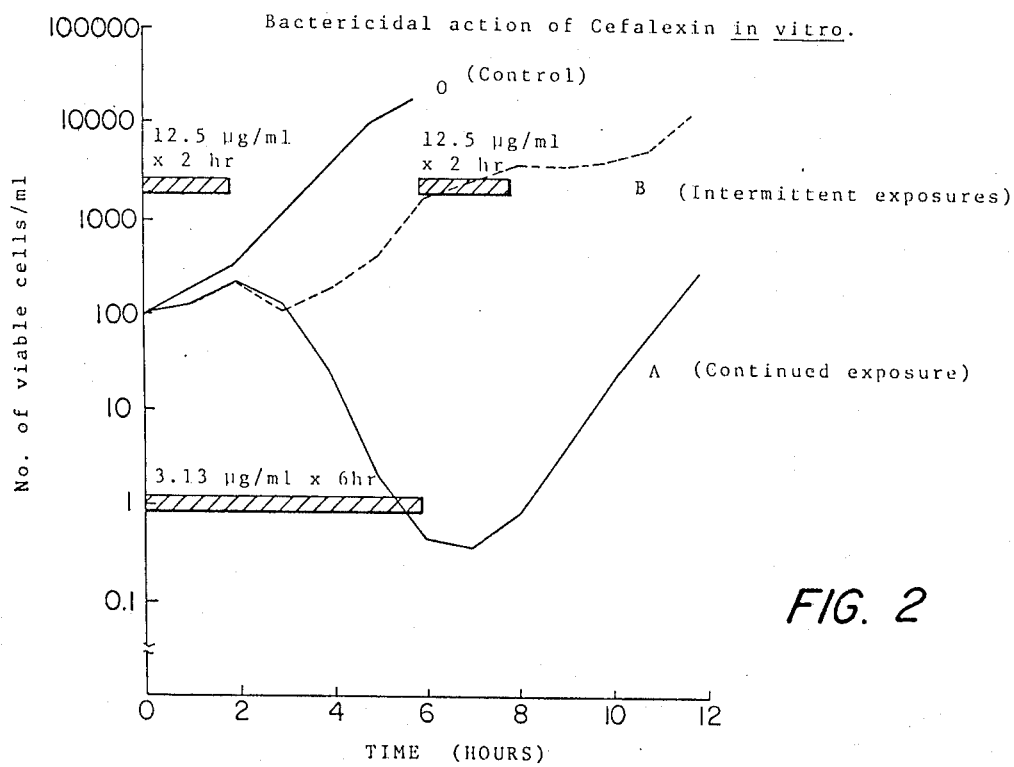

(f) Dual (intermittent) exposure of the bacteria to 12.5 μg/ml of cefalexin each for 2 hours, i.e., from 0 to the 2nd hour and from the 6th to the 8th hour show no remarkable decrease in the number of viable cells, while a continuous exposure for 6 hours to 3.13 μg/ml cefalexin concentration reduces the number of viable cells significantly down to 1% or less (FIG. 2).

(g) Thus, it is concluded that the bactericidal action of cefalexin depends on exposure time rather than the blood level of the drug, insofar as the required MIC is maintained during the exposure.

EXPERIMENT 1 (FIG. 1)

Method (1) *Staphylococcus aureus* 209P (ATCC 6538P) in logarithmic growth period was inoculated in ABM3 (Difco) broth at an inoculum size of $10^5$ cells/ml.

(2) Cefalexin was added to the broth at a concentration of 3.13 μg/ml and allowed to stand for a predetermined exposure time [0 hour i.e., control (Line 0), 2 hours (Line D), 3 hours (C), 4 hours (B) or 6 hours (A)].

(3) The broth was centrifuged to collect bacteria, which was then washed to remove cefalexin, inoculated again in the said medium and cultured for a given time.

(4) The broth medium containing the viable cells was diluted, and a part of the bacterial suspension was spread over nutrient agar plate. After 24 hours propagation, the number of colonies was counted and plotted in terms of the number of viable cells in the original broth medium.

Results (1) Cefalexin killed a definite number of the bacteria, but after removing the drug, the surviving bacteria began to increase.

(2) The minimum number of viable cells and increasing rate of viable cells (recovery) varied depending on exposure time (2 hour exposure showed no minimum, while 6 hours exposure showed minimum of less than 1%).

(3) A remarkable difference was observed between the 4 hour exposure and that of the 6 hour exposure.

EXPERIMENT 2 (FIG. 2)

The same test microorganism was employed and a generally similar procedure was followed in this experiment as described in EXPERIMENT 1, with the exception that:

Cefalexin was added to the broth at a concentration of:

(i) 0 μg/ml (Line O, Control)
(ii) 3.13 μg/ml (Line A) for 6 hours continuously.
(iii) 12.5 μg/ml (Line B) intermittently for 2×2 hours, i.e., 0 to the 2nd hour and the 6th to the 8th hour.

(Exposures are indicated by hatched traversing bars in the figure.)

Results (1) Even at a high exposure concentration of 12.5 μg/ml, discrete exposures for 2 hours with a 4 hour interval, i.e., from 0 to the 2nd hour and from the 6th to the 8th hour, were almost ineffective in decreasing the number of viable cells.

(2) Continuous exposure for 6 hours under 3.13 μg/ml effectively reduced the number of viable cells to a minimum at 8 hour time.

(3) The bactericidal action of cefalexin depended on the exposure time rather than on the concentration under the experimental condition.

2. Blood level of cefalexin in man

In order to avoid the possibility of any unfavorable side effects, it is preferable to keep the blood level at a minimum necessary value for a required period to have an effective and safe treatment of an infection with cefalexin. For the purpose of confirming the reported blood level-time relationships of normal cefalexin, the following Experiment 3 was performed. (See: K. Seiga, Chemotherapy (Japan), 18(6); 899, 1970: H. Nishimura, Saishin Igaku, 24(9); 1983; 1969: R. S. Griffith et al., Clin. Med. 75; 14, 1968: P. Brawn, Applied Microbiology, 16(11); 1684, 1968: and T. S. Thornhill, Applied Microbiology, 17(3); 457, 1969).

EXPERIMENT 3 (FIG. 3)

(1) Normal cefalexin (granules) comprising 200 mg (Line C of the figure), 300 mg (Line B) or 400 mg (Line A) of active ingredient was given orally to 6 apparently healthy volunteers immediately following a meal.

(2) The blood level of cefalexin was measured by assaying antibacterial potency of a blood sample according to a conventional method.

(3) Mean blood levels calculated from the data of each of the 6 volunteers were plotted against every hour from 0 to the 6th hour, after the administration.

Results (1) The blood levels rose rapidly to reach a maximum after 1 to 2 hours.

(2) After 3–4 hours the level fell to ½ of the peak value and after 5–6 hours to 1/10 of the peak value.

(3) Peak values were about 4 μg/ml for the 200 mg dose, about 6 μg/ml for the 300 mg dose and about 7 μg/ml for the 400 mg dose, respectively.

From the above results, it is presumed that even with an exceptionally high dosage of 1000 μg/ml or more, the required standard inhibitory concentration of 3.13 µg/ml for more than 6 hours, would never be attainable by the single administration of normal cefalexin.

The MIC given here (3.13 µg/ml) is the value of most of the clinically isolated strains belonging to *Staphylococcus aureus, Streptococcus haemolyticus* and *Streptococcus pneumoniae*.

Therefore, it is confirmed that this means of extending duration of MIC is not realistic and an alternative method for the purpose should be envisaged.

3. Attempt to make cefalexin long-acting

As a result of the careful scrutinization of the previously described views and discoveries, a necessity for a long-acting preparation of cefalexin is strongly felt. With this preparation, a safe and effective clinical treatment of an infectious disease is made possible.

Although chemical (structural modification) or physiological (e.g., controlling execretion by concurrent use of probenecid) retardation of the action has been contemplated, this has never succeeded in the clinical field.

Therefore, a pharmacokinetical method of retarding absorption is considered to be feasible and is exclusively investigated here.

(A) Time-dependent coating of cefalexin

In an attempt to develop a prolonged releasing or slowly absorbable preparation, 4 kinds of cefalexin granules were coated with ethyl cellulose so as to show 50% dissolution times of 0.5, 1.5, 2.5, and 3.5 hours, respectively when determined by the use of an apparatus described in U.S. Pharmacopeia XIX (ph 2.2 and 7.0; 100 r.p.m.).

The coated granules were given to healthy volunteers and urine excretion rates were measured. From the obtained data, the following facts were found:

(a) Time dependency of the dissolution rates was observed with each of the groups of granules tested in both of the solutions. Only slight differences in the rates were found by differing the pH value.

(b) With the increase in difficulty of diffusion of core drug through the coating layer the dissolution rate decreased.

(c) Only slight differences were observed in the time when the peaks appear in the urinary excretion rates but a significant difference was observed in the urinary excretion itself, attributable to the differences in the diffusion rates of the respective granules.

(d) Total amounts of urinary excretion decreased with the decrease in the diffusion rates of the coated layers, in other words, the more the dissolution rates were delayed by this means, the more the total amount of urinary excretion decreases.

Details of these results are however omitted from the instant description for brevity.

Apart from this, it is already known that cefalexin is absorbed mainly through the limited upper portion of small intestine (duodenum and jejunum: J. S. Welles et al., Anti-microbial Agent and Chemotherapy, 489, 1968, and the present inventors' confirmation through this work).

The results of this experiment suggests a very poor bioavailability of this type of preparation if the thickness of the coated layer is made sufficient enough for retarding the absorption and excretion.

Namely, it is confirmed that a long-acting preparation cannot be realized by means of merely delaying the disintegration rate with a coating layer having pH-independency. In other words, a preparation with a time-dependent coating does not contribute to the effective treatment of the infectious disease. The remaining portion of the drug in the core granules which dissolve after the passage of granules through the upper intestine might be wasted in feces.

(B) pH-Dependent coatings

On the basis of an experience of two of the present inventors (H. Maekawa et al., Yakuzaigaku, 30 [2] 94-101 and 102-110 (1970) reports that enteric coated granules, when administered immediately after a meal, travel continuously and gradually from the stomach to the upper intestine for several hours after administration, and the granules placed there disintegrate rapidly), another pharmacokinetical measure of making cefalexin long-acting is envisaged. The following series of experiments was performed wherein the coating of cefalexin granules with materials having pH-dependent solubility was investigated and evaluated.

Figure 4A:
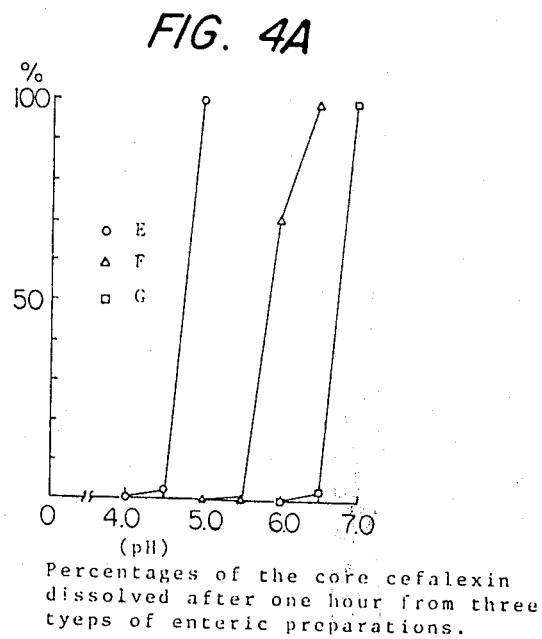
FIG. 4A is a graph indicating percentage dissolution after one hour of enteric coated granules having various dissolution pHs.
Figure 4B:
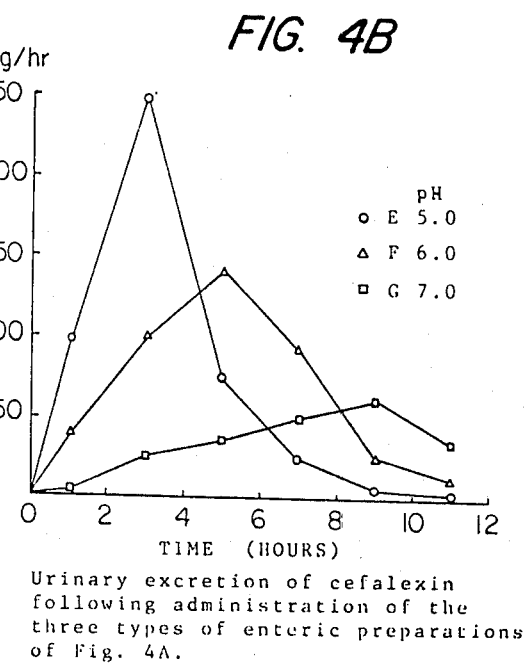
FIG. 4B is a graph indicating rates of urinary excretion of cefalexin after administration of the same granules.

EXPERIMENT 4 (FIGS. 4A and 4B)

As coating materials which dissolve in the alkaline medium, i.e., in the intestine, hydroxypropylmethylcellulose phthalate (HPMCP), Eudragit L and Eudragit S (Trade names of coating materials comprising copolymer of methylmethacrylate and methacrylic acid) were picked to be tested.

The enteric coatings are characterized by their dissolution pH. This term, used here, is defined as the lowest pH value at which the coatings dissolve rapidly to release the cefalexin in the coated cefalexin preparation (FIG. 4A).

The three kinds of enteric granular having dissolution pHs of about 5.0, 6.0 and 7.0 designated by E, F and G were prepared by coating normal cefalexin granules with HPMCP, Eudragit L and S, as coating materials, respectively.

The dissolution rates in various buffer solutions of varying pH, and the urinary excretion rates of humans to which these three were administered are measured in a manner as previously described, respectively, to obtain the results shown in FIGS. 4A and 4B which are summarized below.

Results (FIG. 4B)

(a) Granules F having a dissolution pH around 6 show an urinary excretion rate-time curve having a peak value at approximately five hours after administration.

(b) A high recovery (average 83% of the given dose) of the drug from urine was observed, suggesting efficient absorption and excretion.

(c) Granules G (dissolution pH, around 7) have a peak at 9 hours after administration but with a remarkable decrease in the total amount of urinary excretion.

(d) The curve for granules E having a dissolution pH around 5 rises comparatively rapidly and falls quickly.

(e) Both of the latter two were found to be not suited for the long-acting preparations of cefalexin.

(f) In these cases, the thickness of the coating layers had less influence on the velocity of release than the pH dependent properties of coating material.

These results suggests that the optimum dissolution pH is between 5.5 and 6.5, and more preferably around 6 in order to keep the blood level at a sufficiently high value for a required period of time and to preserve the relatively high bioavailability.

(C) Aortal blood level of cefalexin obtainable with this preferred preparation

Figure 3:
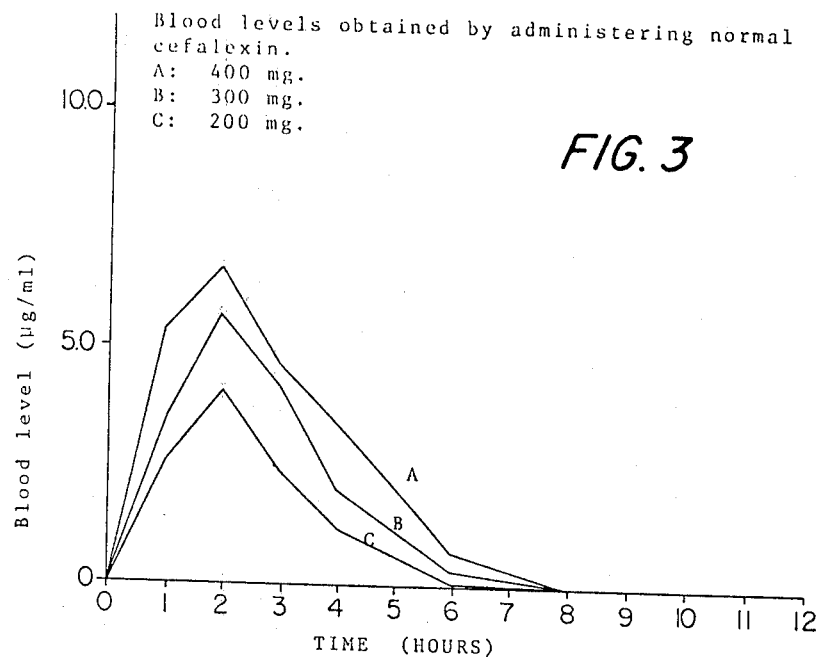
FIG. 3 is a graph representing the blood levels of cefalexin in man vs. time after oral administration of normal cefalexin.

In order to confirm the actual blood level obtainable by administering this preferred dosage-form, a series of experiments are performed to obtain the results summarized in FIG. 5, which are compared with those of Experiment 3 and the curves in FIG. 3.

EXPERIMENT 5 (FIG. 5)

(1) Enteric-coated granules containing 300 mg (Curve C), 600 mg (Curve B) or 900 mg (Curve A) of cefalexin having a dissolution pH of 6.0 were given orally to 6 apparently healthy volunteers immediately after a meal in the cross-over method.

(2) Measurement of the blood levels and delineation of the mean blood level vs. time curve were made in accordance with the methods described in Experiment 3.

Results (a) The peak blood levels appeared at 6 hours after administration.

(b) The blood level which exceeds ½ of the peak value, extended over 6 hours (Curve B).

(c) The time lag (rise-up time) to reach ½ of the peak value was about 3 hours (Curve B).

(d) The above observation is also applicable to the two other dosages (300 mg and 900 mg).

(D) Time lag for reaching the required blood level (rise-up time) and its reduction The said enteric-coated cefalexin, however, shows a peak of blood level after five to six hours from administration, and the time spent for reaching the required blood level is too long (e.g., 3 hours) to expect an effective clinical response.

Since the patient who requires an antibacterial agent is suffering from an infectious disease and usually an urgent action of the agent would also be imperative, this length of the time lag might sometimes be a very great disadvantage.

In order to overcome this disadvantage of the enteric-coated preparation used alone by reducing the time lag, a concurrent use of quickly absorbable cefalexin with this preparation is contemplated. A physician who prescribes the drug is, however, not always aware of the proper use of these two types of dosage forms, particularly, of its appropriate ratio to be prescribed in order to attain the required blood level and to maintain the level for the required period.

In view of the above, a combined dosage-form of enteric-coated preparation with normal cefalexin in a most preferred ratio pre-mixed by a pharmaceutical manufacturer, is considered to be the most preferred and practical.

(E) Determination of optimum range of the mixing ratio

The results of Experiments 3 and 5, illustrated in FIGS. 3 and 5, indicate proportional relationships between the blood levels at respective times during the measurements and the amounts of the administered drug. In order to provide basis for designing the preferred preparation, the information contained in FIGS. 3 and 5 are analyzed to illustrate mean levels of cefalexin in blood corresponding to each one milligram of the drug, shown as plots in FIG. 6.

Curves A and B of FIG. 6 are obtained from the data of FIGS. 3 and 5 and are shown as if they were real representations of the blood levels corresponding to the normal and enteric preparations, respectively, but are delineated according to model equations devised by mathematical simulation so that both of the curves are in substantial conformity with curves enveloping the respective plots.

From the information contained in FIG. 6, time changes in blood levels of cefalexin of men who took three typical mixed dosage-forms containing 500 mg of cefalexin in varied ratios of normal/enteric cefalexin i.e., A: normal/enteric=70/30, B: normal/enteric=50/50 and C: normal/enteric=30/70, are also calculated and delineated as shown in FIGS. 7A, 7B and 7C, respectively.

Figure 8:
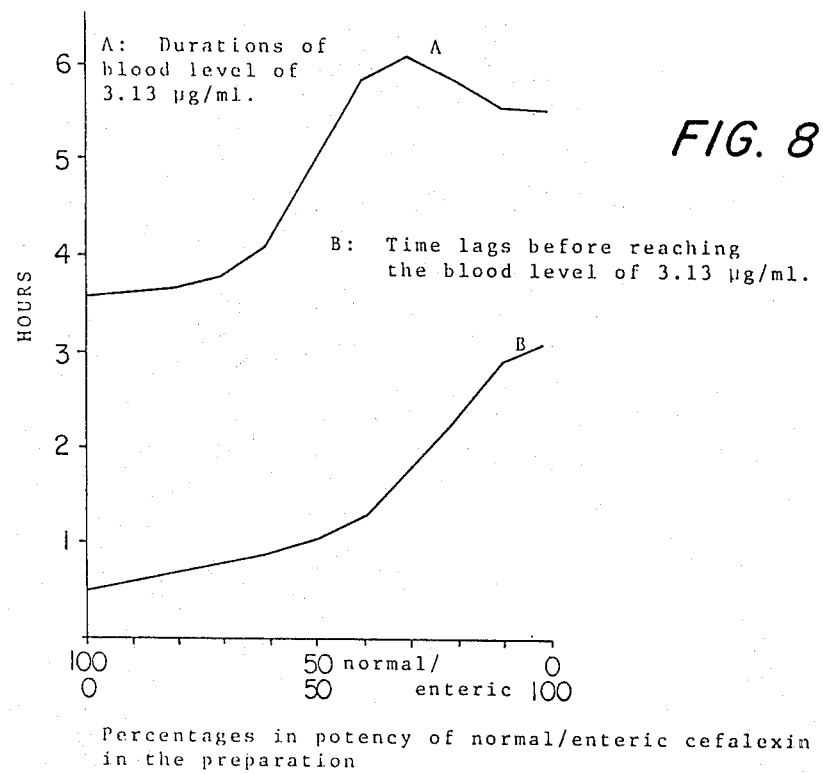

Duration of the standard inhibitory concentrations for preparations containing both ingredients in terms of potency ratios which extend over the full range (i.e., 0–100% vs. 100–0% with 10% increments) is calculated to delineate a curve A shown in FIG. 8 from a composite curve derived from FIG. 6 in order to confirm the fact that the duration starts to prolong itself as to a preparation containing the enteric ingredient in an amount of at least 40% and this prolongation becomes remarkable for one containing the enteric ingredient in an amount of at least 50%.

On the other hand, time lags (rise-up times) spent for reaching or required for attaining the effective blood level for preparations of various potency ratios are also calculated to present a curve B shown in FIG. 8 obtained by connecting plots.

From the information contained in FIG. 8 (Curve B), it is confirmed that the rise-up time obtained with a preparation containing at least 15% of normal cefalexin significantly differs from that obtained with a 100% enteric preparation, and this advantageous feature is remarkably improved with a preparation containing the normal cefalexin in an amount of at least 20%. The ingredient may be increased up to 60% from the aspect of the preferred, short time lag.

As a consequence of the realistic compromise between the just mentioned aspect and that of the effective prolongation of the duration, it is found that the content of the conventional cefalexin in this combined preparation must be 15 to 60%, preferably 20–50% and more preferably 25–40%, and that of the enteric ingredient must be 40 to 85%, preferably 50–80% and more preferably 60–75% in terms of potency.

(F) Confirmation of the blood level in vivo

Figure 9:
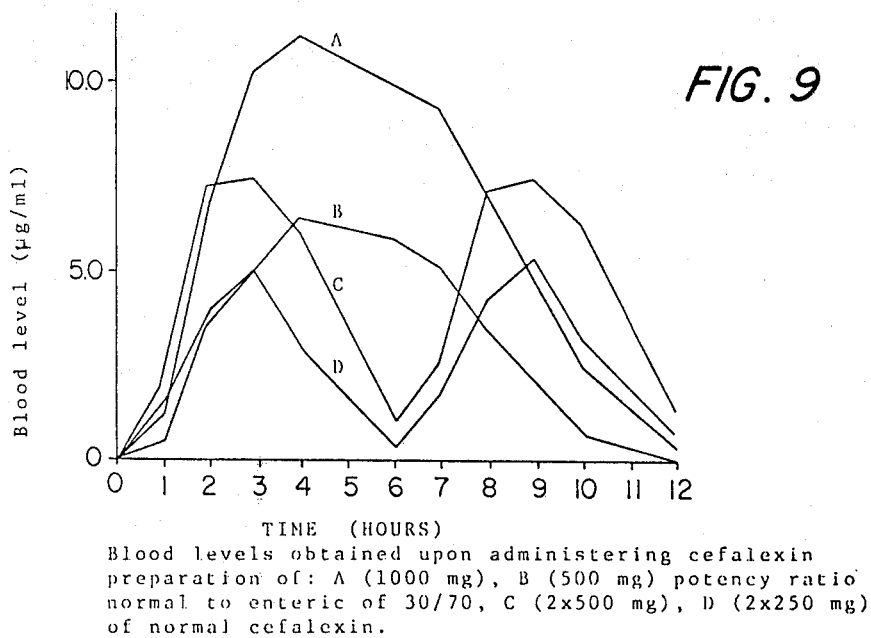
FIG. 9 is a graph indicating the blood levels obtained over a 12 hour period following administration of the combined preparations at a potency ratio of normal to enteric of 30/70 as compared with those levels obtained following administration of normal cefalexin in two doses spaced 6 hours apart.
Figures 1, 9:
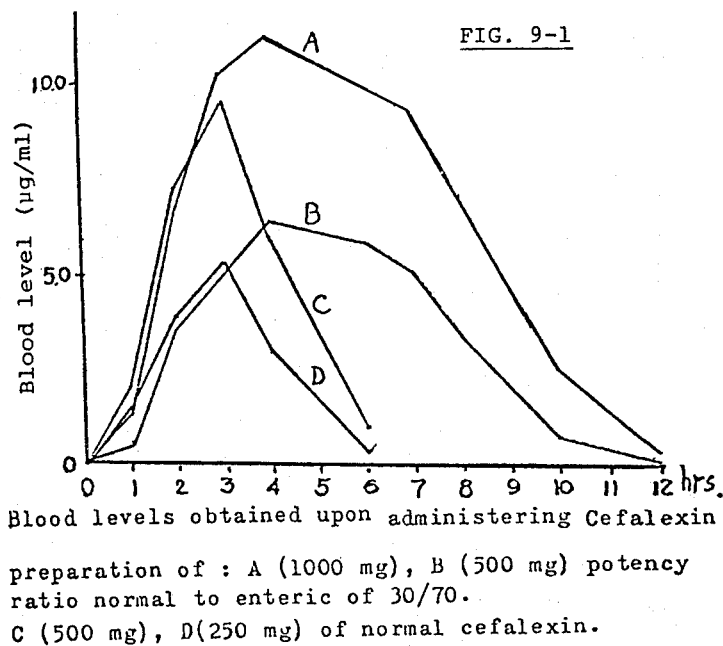
Figures 2, 9:
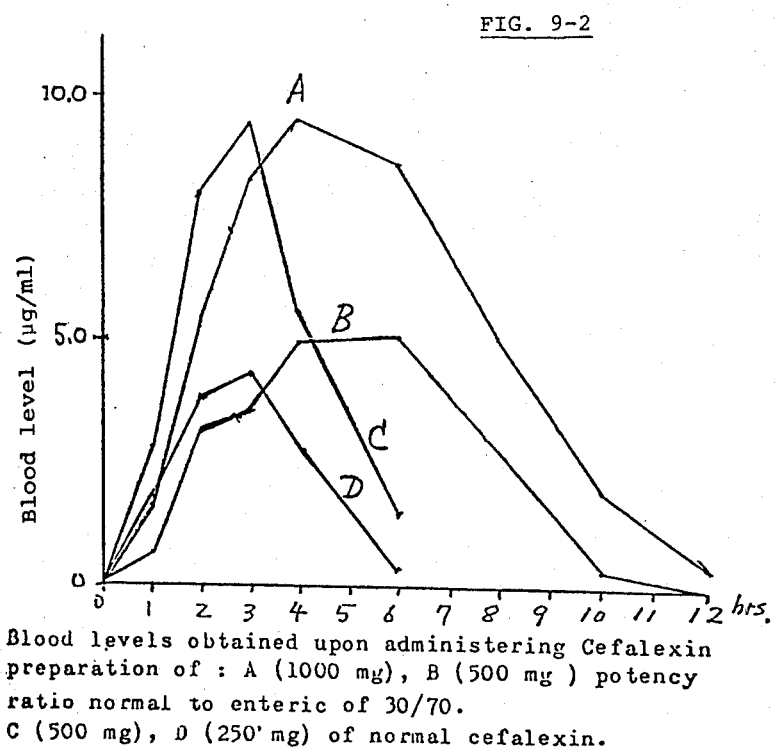

As can be seen from the curve shown in FIG. 7C, the duration of the desired blood level over 6 hours, obtained with the combined preparation of normal/enteric=30/70, seems to be the most realistic considered from both aspects, and this has been confirmed by a clinical investigation on human subject mentioned below and which is illustrated in FIG. 9.

When a unit-dosage form of 500 mg or 1000 mg of cefalexin in the just mentioned normal/enteric ingredient potency ratio was given orally to apparently healthy volunteers immediately after a meal, the desired blood level (3.13 µg/ml, curve B or 6.25 µg/ml, curve A; average of 8 men) was maintained over a period of 6 hours continuously, from about hour 1.5 through hour 7.5 after administration.

In contrast to the above results, with a prescription which indicates administrations at intervals of six hours containing conventional preparations containing 250 mg or 500 mg of cefalexin, the same blood levels were attained and kept only intermittently from the 2nd through 4th hours and from the 8th through the 10th hours after the first administration as shown by curve C or D in FIG. 9. Even with the additional administration at the 6th hour after the first one, continuous duration of the blood level cannot be attained.

The same reference characters A, B, C and D are also used in FIGS. 9-1 and 9-2, for indicating curves having the same significances.

In FIG. 9-1, corrections are made on the information in FIG. 9, by supplementing the curves C and D by missing values in the blood levels which had been erroneously and unintentionally disregarded when FIG. 9 was drawn. The blood levels following the 2nd administration of normal cefalexin are omitted.

The corrections, however, only raised the peak values but left the durations of the desired blood levels obtained by administering normal cefalexin intact, and therefore did not affect the stated advantageous feature.

The results obtained with a more extensive investigation on 20 volunteers performed in compliance with the cross-over method are presented in FIG. 9-2, wherein the blood levels are somewhat lowered as a whole as compared with those in the preceding investigation but the relativity among the respective curves in FIG. 9 or 9-1 is substantially retained as it stands.

The unequal blood levels are presumed to be attributable to the difference in, for instance, constitution, physical conditions, dieting habit, and quality and quantity of meal taken prior to the administration of the individual volunteer.

The grouping of the participated volunteers and the time when the respective investigations were performed, might also have some effect on the results of the observation.

From the information contained in FIGS. 9, 9-1 and 9-2 in view of those in FIGS. 1 and 2, it is apparent that the cefalexin preparation of this invention is more effective than the conventional cefalexin preparation when the same total dosage was given according to the current indication.

(G) Clinical response in terms of viable cells in urine

Figure 10:
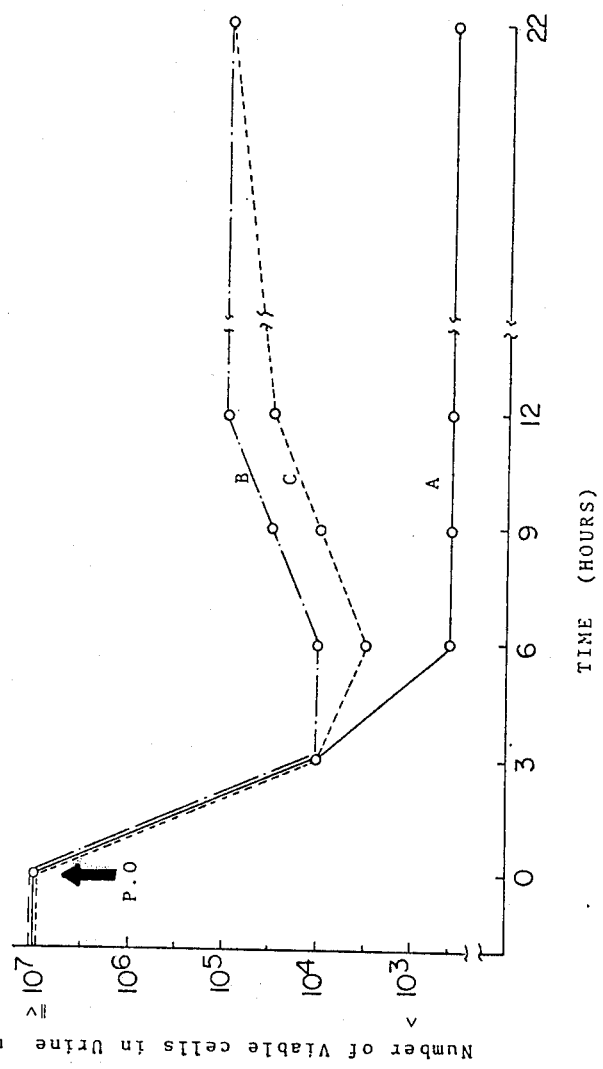
FIG. 10 is a graph indicating the number of viable bacteria in urine of patients, suffering from asymptomatic bacteriuria, following administration of three cefalexin preparations.

Another comparative clinical investigation was made on the bactericidal activity (effective inhibition ability) of the combined preparation having the preferred potency ratio mentioned in the preceding section F, to give a result summarized in FIG. 10.

The combined preparation (500 mg, curve A) and two normal preparations (250 mg, curve B and 500 mg, curve C) were administered immediately after a meal to 9 patients, 8 patients and 5 patients, respectively who had been suffering from asymptomatic bacteriuria caused by at least one of the various strains which belong to genera of Escherichia, Pseudomonas, Streptomyces, Klebsiella, Retigeralla and Enterobacter, and the number of viable cells of the bacteria in their urine excreted in predetermined intervals after the oral administration (indicated in FIG. 10 by a thick arrow with the letter P.O.), were counted in a conventional assaying method to present the curves in FIG. 10 which are means values of the patients.

It is to be noted herein that a virtually complete suppression was made with the combined preparation even after 22 hours from the administration, whereas both of the normal preparations failed in attaining a sufficient suppression.

A series of ancillary experiments conducted for investigating the improved clinical response of the preparation of this invention for animals (dogs and rabbits), disclosed a very poor bioavailability of this preparation. There was found no retarded absorption and the major portion of the administered drug was excreted into feces before being absorbed; no expected rise in blood level was found and no extension in its duration.

It was presumed that the failure in the attempt for the application on animals was mainly due to the differences in the structures of digestive organs of these animals from that of humans, particularly to the short lengths of their absorption sites for the drug.

Therefore, it is safely concluded that the previously described design of this preparation is solely suited for human use. The details of the animal experiments were omitted for brevity.

PREFERRED EMBODIMENTS OF THIS INVENTION

The preparation of this invention is in a form of powder, beads, granules, microcapsules, preferably in a unit dosage form, for example, capsules, tablets or granules packed in strip-packages.

The unit-dosage preparation usually contains 50 mg to 2000 mg of cefalexin in terms of potency, preferably between 500 mg to 1000 mg when the desired blood level is 3.13 μg/ml or 6.25 μg/ml for adult use.

The ratio in terms of potency of normal/enteric ingredients is between 15:85 and 60:40, preferably between 50:50 and 20:80, more preferably between 40:60 and 25:75, and most preferably 30:70.

The enteric ingredient of this preparation is coated with material which dissolves to disintegrate the core granules in the upper intestine, i.e., soluble in a high pH region. Its dissolution pH is preferably between 5.5 and 6.5, and more preferably about 6.0.

A preferred example of the coating material is a copolymer of methylmethacrylate and methacrylic acid (Eudragit L). One skilled in the art may obtain another coating material having the preferred dissolution pH by admixing two or more other materials.

According to this invention, the preparation is (A) a mixture of each of the normal and enteric dosage forms, or (B) two separate dosage forms packed in separate containers to be mixed by a druggist, doctor or patient.

The mixed preparation (A) in unit dosage form is more convenient for a patient. Doctors and druggists can, however, make more accurate prescriptions for a specific patient e.g., children, if they use the two separate dosage forms (B) in separate containers As indicated previously herein the dissolution of the coating is more dependent upon the dissolution pH than upon coating thickness. In general, therefore, the weight ratio of coating material to particulate cefalexin is not critical. It will generally range in the amount of 1:5 to 1:2.

In both cases, most of the patients suffering from infections caused by bacteria sensitive to cefalexin, satisfactorily respond to an effective amount of the two component preparation at the ratio specified above.

The sustained release preparation (A) or the sustained release prescription of (B) can be administered to a patient suffering from bacterial infections caused by a sensitive bacteria at 12 hour intervals, each preferably immediately after a meal.

EXAMPLES

These examples are given to illustrate this invention in detail, but are not intended to restrict the scope thereof.

(a) Normal cefalexin granules:

A mixture of cefalexin (1117 g), lactose (270 g), and corn starch (97 g) is kneaded well with a 8% starch paste (500 g), and the mixture is granulated by a cylindrical granulator, followed by drying at 60° C. for 1 hour.

The dried granules are crushed by a Fitzpatrick mill and sieved to give uniform granules of 16 mesh to 24 mesh.

(b) Enteric coated granules:

The normal cefalexin granules a) (1000 g) are placed in a coating pan (40 cm diameter) and are coated in a conventional method by spraying an alcoholic solution of Eudragit L (containing 52 g of Eudragit L and 52 g of talc in 1000 g of ethanol: total 3500 g) to give uniformly coated granules.

(c) Assay of antibacterial potency:

The potency of each of the coated granules and of the normal cefalexin is measured for determining an accurate mixing ratio.

(d) Unit-dosage form in strip-package:

The normal cefalexin granules (150 mg in potency; about 205 mg in actual amount) and enteric coated cefalexin granules (350 mg in potency; about 650 mg in actual amount) described in the preceding paragraphs a) and b), are mixed and filled in a pouch by a conventional strip-packaging machine. This preparation is used to confirm the advantages of this invention.

(e) Unit-dosage form in hard gelatine capsules:

The mixture of the granules as prepared in paragraph d) is filled in hard gelatine capsules (each containing 125 mg in total potency).

ATTENDANT ADVANTAGES OF THIS INVENTION (A) Many strains of bacteria have a similar time-dependency of response against cefalexin when compared with the bacteria used in this investigation, i.e., *Staphylococcus aureus* strain 209P, and 9 other strains of *Staphylococcus aureus* and 6 strains of *Escherichia coli*. Therefore, the preparation or the method of this invention is expected to be clinically effective against some infectious disease which is insufficiently treated with the normal cefalexin preparations. Thus, this invention will explore a new field of clinical use of cefalexin without creating difficulty in the prescription and administration.

(B) From another aspect, this invention reduces the therapeutic period and therefore the necessary amount of cefalexin, while maintaining the same bactericidal effect and minimizing the possible danger of side effects of conventional cefalexin preparations.

(C) Moreover, it enables twice daily administration of the drug at 12 hour intervals without reducing the effect, thus it does not interrupt the patient's sleep at midnight as does the conventional cefalexin prescribed for administration 4 times daily at 6 hour intervals.

(D) Some of the side effects, for example, stomach disorder caused by the passage of cefalexin through the stomach can be reduced by this invention.

What is claimed is:

1. A long-acting cefalexin preparation which comprises normal cefalexin which dissolves rapidly in the stomach, and coated particulate cefalexin which does not dissolve in the stomach but dissolves rapidly in the upper intestine, wherein the said coated portion is coated with a copolymer of methylmethacrylate and methacrylic acid which has a dissolution pH of from 5.5 to 6.5, and wherein the potency ratio of the normal cefalexin to the coated portion is between 40:60 and 25:75.

2. A preparation as claimed in claim 1 wherein the potency ratio is approximately 30:70.

3. A preparation as claimed in claim 1 wherein the dissolution pH is approximately 6.0.

4. A preparation as claimed in claim 1 wherein the particulate cefalexin is in the form of powder, beads, granules or microcapsules.

5. A preparation as claimed in claim 1 in a unit dosage form.

6. A preparation as claimed in claim 5 in the form of capsules.

7. A preparation as claimed in claim 5 in the form of tablets.

8. A preparation as claimed in claim 5 in the form of beads, granules or microcapsules contained in strip-packages.

9. A preparation as claimed in claim 5 wherein the unit dosage form contains 50 to 2000 mg of cefalexin in terms of potency.

10. A preparation as claimed in claim 9 wherein the unit dosage form contains 500 to 1000 mg of cefalexin in terms of potency.

11. A method for treating a human infection caused by bacteria sensitive to cefalexin which comprises administering to a human suffering from said infection immediately following a meal a bactericidally effective amount of a preparation as claimed in claim 1.

12. A method according to claim 11 wherein the potency ratio is about 30:70.

13. A method according to claim 11 wherein the dissolution pH is about 6.0.

14. A method for treating a human infection caused by bacteria sensitive to cefalexin which comprises administering to a human suffering from said infection immediately following a meal a pharmaceutical composition in compressed tablet form according to claim .

* * * * *